United States Patent [19]

Di Mino et al.

[11] Patent Number: 5,190,037
[45] Date of Patent: Mar. 2, 1993

[54] HIGH-POWER CORONA DISCHARGE BEAM THERMOTHERAPY SYSTEM

[75] Inventors: ALfonso Di Mino; Andre Di Mino, both of Woodcliff Lake, N.J.

[73] Assignee: ADM Tronics Unlimited, Inc., Northvale, N.J.

[21] Appl. No.: 826,105

[22] Filed: Jan. 27, 1992

Related U.S. Application Data

[63] Continuation-in-part of Ser. No. 779,841, Oct. 21, 1991.

[51] Int. Cl.$^5$ .............................................. A61N 1/02
[52] U.S. Cl. .................... 128/422; 128/410 R; 128/783; 128/800
[58] Field of Search .................. 128/422, 419 R, 800, 128/804, 399, 783, 423 R

[56] References Cited

U.S. PATENT DOCUMENTS

| | | | |
|---|---|---|---|
| 3,617,684 | 11/1971 | Di Mino | 219/121.11 |
| 3,676,633 | 7/1972 | Di Mino | 219/121.36 X |
| 3,991,770 | 11/1976 | LeVeen | 128/804 |
| 4,249,537 | 2/1981 | Lee et al. | 128/422 |
| 4,531,524 | 7/1985 | Mioduski | 128/422 |
| 4,667,677 | 5/1987 | Di Mino | 128/419 R |
| 4,676,258 | 6/1987 | Inokucki et al. | 128/804 |
| 4,865,047 | 9/1989 | Chou et al. | 128/804 X |
| 4,945,912 | 8/1990 | Langberg | 128/804 X |

Primary Examiner—Lee S. Cohen
Assistant Examiner—Jeffrey R. Jastrzab
Attorney, Agent, or Firm—Michael Ebert

[57] ABSTRACT

A corona discharge beam thermotherapy system for veterinary applications adapted to project the beam onto the skin surface of an animal overlying a problem region, the beam serving to relieve pain and to obtain other beneficial effects. The system includes an energy-generating unit having a power in excess of 25 watts in which a radio-frequency carrier is overmodulated by an audio frequency signal to produce periodic bursts of radio-frequency energy whose repetition rate corresponds to the frequency of the signal. The output of the unit is fed by a flexible coaxial cable to a tank circuit tuned to the carrier frequency and housed within the barrel of a portable applicator gun. Supported within the barrel and coupled to the tank circuit is a discharge electrode whose tip is adjacent the mouth of the barrel. The electrode is formed by a helical wire, one end of which is coupled to the tank circuit, the other end defining the tip. The length of the wire is such as to create an antenna from which substantially all of the energy supplied thereto is radiated from the tip to create a corona beam of high strength that is effective in treating animals.

11 Claims, 2 Drawing Sheets

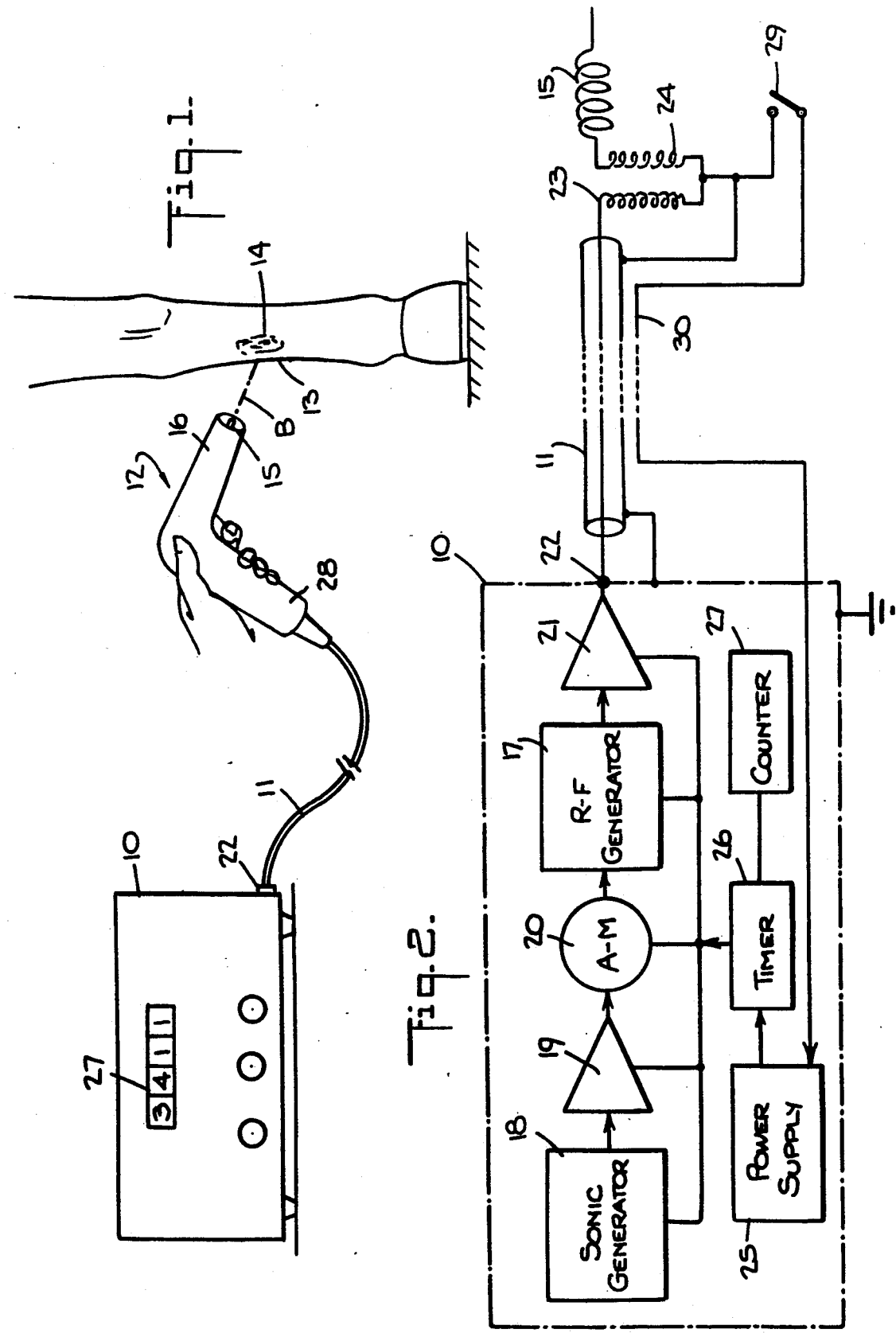

HIGH-POWER CORONA DISCHARGE BEAM THERMOTHERAPY SYSTEM

RELATED APPLICATION

This application is a continuation-in-part of our copending application Ser. No. 779,841, filed Oct. 21, 1991, entitled "Corona Discharge Beam Thermotherapy System," the entire disclosure of which is incorporated herein by reference.

BACKGROUND OF INVENTION

1. Field of Invention

This invention relates generally to thermotherapy, and in particular to a high-power corona discharge thermotherapy system for relieving pain and obtaining other salutary effects in relatively large animals, in which the skin surface of the animal being treated overlying a problem region is subjected to a corona discharge beam derived from periodic bursts of radio-frequency energy whose repetition rate is at a sonic frequency.

2. Status of Prior Art

The term "problem region" as used herein refers to a set of muscles, an arthritic joint or any other region underlying the skin of an animal which is causing difficulty and which lends itself to treatment by thermotherapy.

Of greatest prior art interest is the Di Mino U.S. Pat. No. 4,667,677, which discloses a unit for generating a corona discharge beam and for projecting this beam toward the skin surface of a living body (human or animal) overlying a problem region, the beam serving to relieve pain and gain other salutary effects. The Di Mino unit includes a radio-frequency carrier generator which is overmodulated with an audio-frequency signal to produce periodic bursts of radio-frequency energy whose repetition rate corresponds to the frequency of the signal. These bursts are stored in a tank circuit coupled to the output of the modulated radio-frequency carrier generator. Connected by a short cable to the output of the tank circuit is a hand-held discharge electrode from which is projected a corona discharge beam, the electrode being manipulated by the operator to scan the skin surface to be treated.

Our above-identified copending application is directed to an improvement over the unit disclosed in the Di Mino patent. In this improvement, the output of the unit is fed by a flexible coaxial cable to a tank circuit tuned to the carrier frequency and housed within the barrel of a portable applicator gun on whose grip is mounted a trigger switch operatively connected to the unit. Supported within the barrel and coupled to the tank circuit is a relatively short and straight discharge electrode whose tip is adjacent the mouth of the barrel. When an operator holding the gun actuates the trigger switch, the unit is turned out and a corona discharge beam is then projected from the electrode tip, the operator positioning the gun to direct the beam toward the skin surface to be treated.

The power output of the system disclosed in our copending application is relatively low (i.e., 5 to 15 watts). And while we have found this system to be highly effective in treating human patients, it is less efficacious when used on large animals, such as horses, for such treatment requires a corona beam of greater strength.

In seeking to meet this requirement, we increased the power of the system to a level above 25 watts, such as 40 or 50 watts, well above the power appropriate for human patients. But we found that the resultant corona discharge beam was still not of adequate strength. However, by providing a much longer electrode (approximately 9 inches in length), the resultant strength of the corona discharge beam was brought up to an acceptable level.

This elongated electrode presented a problem, for it could not be included in the barrel of the portable applicator gun disclosed in our copending application. The reason for this is that the barrel housed the tank circuit of the system, and the only way we could include an elongated straight electrode in the barrel and couple it to the tank circuit was to greatly increase the length of the barrel so that it would accommodate the electrode. A barrel of this length would result in an applicator rifle, not a gun, and would be altogether impractical, for it is essential that the applicator be easily manipulated by the operator.

SUMMARY OF INVENTION

In view of the foregoing, the main object of this invention is to provide a high power corona discharge beam thermotherapy system for veterinary applications to treat animals such as horses.

More particularly, an object of this invention is to provide a system of the above type which includes a portable applicator gun having an elongated discharge electrode supported within the relatively short barrel of the gun, a corona discharge beam being projected from the tip of the electrode and being directed toward the skin surface of the animal being treated which overlies a problem region in the animal.

Also an object of the invention is to provide an electrode in a portable applicator gun of the type constituted by a helical wire which creates a high-gain antenna for radiating the energy applied thereto from the tip of the electrode.

Briefly stated, these objects are attained in a corona discharge beam thermotherapy system for veterinary applications adapted to project the beam onto the skin surface of an animal overlying a problem region, the beam serving to relieve pain and to obtain other beneficial effects. The system includes an energy-generating unit having a power in excess of 25 watts in which a radio-frequency carrier is overmodulated by an audio frequency signal to produce periodic bursts of radio-frequency energy whose repetition rate corresponds to the frequency of the signal.

The output of the unit is fed by a flexible coaxial cable to a tank circuit tuned to the carrier frequency and housed within the barrel of a portable applicator gun. Supported within the barrel and coupled to the tank circuit is a discharge electrode whose tip is adjacent the mouth of the barrel. The electrode is formed by a helical wire, one end of which is coupled to the tank circuit, the other end defining the tip. The length of the wire is such as to create an antenna from which substantially all of the energy supplied thereto is radiated from the tip to create a corona beam of high strength that is effective in treating animals.

OUTLINE OF DRAWINGS

For a better understanding of the invention as well as other objects and further features thereof, reference is made to the following detailed description to be read in conjunction with the accompanying drawings, wherein:

FIG. 1 illustrates the basic components of a high-power corona discharge beam thermotherapy system for veterinary applications in accordance with the invention;

FIG. 2 is a block diagram showing the various stages of the energy-generating unit included in the system and the applicator gun coupled to the output of the unit;

DESCRIPTION OF INVENTION

The Basic System

Figure 4:
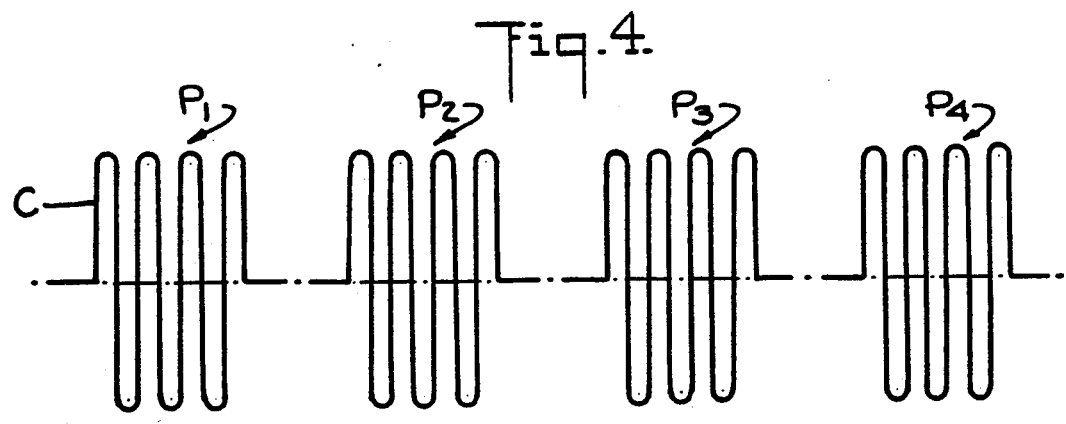
FIG. 4 illustrates the waveform of the bursts of radio-frequency energy produced in the energy generating unit.

Referring now to FIG. 1, a system in accordance with the invention makes use of an energy-generating unit 10 which yields periodic bursts of radio-frequency energy whose repetition rate is at a sonic frequency. This energy is applied via a long, flexible coaxial cable 11 to a hand-held portable applicator gun 12 within whose barrel 16 is mounted a discharge electrode 15 from which is projected a corona discharge beam B. Beam B is directed toward the skin surface 13 of an animal that overlies a problem region 14. By way of example, the drawing shows the leg of a horse.

The tip of electrode 15, which is adjacent the mouth of gun barrel 16, is placed within a few centimeters of the skin. The distance between the electrode tip and the skin is such that the clearly visible portion of the corona discharge beam is slightly spaced from the skin, but the less visible portion which projects therefrom engages the skin. The energy is absorbed by the underlying tissue in the problem region 14 of the animal and converted into therapeutic heat. Because of the corona discharge beam, the zone of engagement is small, and in order to irradiate a relatively large skin area, the beam is scanned over this area so that the entire problem region therebelow is subjected to treatment.

A corona discharge is a highly active glow region surrounding a discharge electrode. When the electrode is the tip of a wire as in the present case, this glow region extends a short distance beyond this point. Assuming the wire is negatively charged, the free electrons in the air in the region if the intense electric field surrounding the wire gains energy in this field to produce positive ions and other electrons by collision. In turn, these new electrons are accelerated and produce further ionization. This cumulative process results in an electronic avalanche in which the positive ions are accelerated toward and bombard the charged wire. As a consequence of such ionic bombardment, secondary electrons are ejected from the tip of the electrode which act to sustain the corona discharge.

When the voltage applied to the discharge electrode is elevated to a level exceeding the point at which a stable corona discharge is maintained, the air dielectric then completely breaks down to cause a spark discharge. In order to produce a corona discharge, the peak voltage on the discharge electrode must be relatively high but below the level resulting in a spark discharge.

The continuous application of a low radio-frequency energy of relatively low power will not result in a corona discharge. But because in the energy-generating unit 10, the continuous radio-frequency carrier is produced in bursts which shock excite a tank coil included in the unit, the resultant energy surges have a peak amplitude sufficient to produce a sustained corona discharge beam.

The Energy Generating Unit

Referring now to FIG. 2, the energy generating unit 10 includes a radio-frequency generator 17 producing an R-F carrier lying in the low frequency range of 200,000 to 300,000 Hz. In practice, this generator is frequency controlled by a piezoelectric crystal oscillator operating, at, say, 200 KHz, the carrier generator also being stabilized as to amplitude. A conventional low radio-frequency generator may be used for this purpose.

Also included in the unit is an audio-frequency generator 18 operating in the audio-frequency range of 3000 to 5000 to produce a sonic signal. This is amplified in amplifier 19 and applied to an amplitude modulator 20, which is so connected to radio-frequency generator 17 as to effect amplitude modulation of the R-F carrier. Audio-frequency generator 18 is preferably a shielded, solid-state, transistorized oscillator.

In amplitude-modulation, the amplitude of the radio-frequency carrier is varied in accordance with the signal, the resultant modulated wave containing side bands that are the sum and difference of the carrier and signal frequencies. If the modulation index "M" is zero, no signal information is conveyed to the carrier. When, however, M=1 (100% modulation), then in the case of a sinusoidal carrier wave, the envelope of the carrier varies from zero to twice the value of its unmodulated amplitude. But if "M" exceeds unity, the carrier is then overmodulated, as a consequence of which the carrier is periodically interrupted at a repetition rate in accordance with the audio-frequency signal.

In the present invention, as shown in FIG. 4, the radio frequency carrier C is overmodulated by the sonic frequency signal, this resulting in periodic bursts $P_1$, $P_2$, $P_3$, etc., of radio-frequency energy whose repetition rate is at the sonic frequency. These bursts of energy from R-F generator 17 are applied through an output amplifier 21 to the output jack 22 of the energy-generator unit.

Plugged into output jack 22 of the energy generating unit 10 is one end of coaxial cable 11 which connects the output of the unit to the tank coil 23 of a tank circuit housed within the barrel 16 of the applicator gun, the tank coil being tuned to the carrier frequency of the unit. Tank coil 23 is inductively coupled to an ouput coil 24 to which is connected the discharge electrode 15 which is in a helical form. It is to be noted that the outer shielding conductor of the coaxial cable 11 is grounded, the inner conductor connecting one end of the tank coil 23 to output jack 22, the other end of the tank coil and the corresponding end of the output coil being connected to the grounded conductor. Because of this arrangement, there is no radiation from the coaxial cable.

Because tank coil 23 is shock excited by the bursts $P_1$, $P_2$, etc., of the radio-frequency energy, the resultant damped wave surges in coil 23 have a high peak amplitude, and this causes the desired corona discharge to produce a beam which is both visible and audible. The reason it is visible is that the corona beam in the region adjacent the electrode tip produces a blue glow, and the reason it is audible is that the bursts of energy are at a sonic rate and therefore can be hard. Because the system is for veterinary applications mostly to treat sizable animals, such as horses, the power output of the system must be at least 25 watts and is preferably between about 40 to 50 watts. We have found that when this high power system includes an elongated electrode as hereinafter described in a helical form functioning as an antenna, the resultant heat energy induced in the painful problem region is capable of relieving this pain within a relatively short period.

Figure 5:
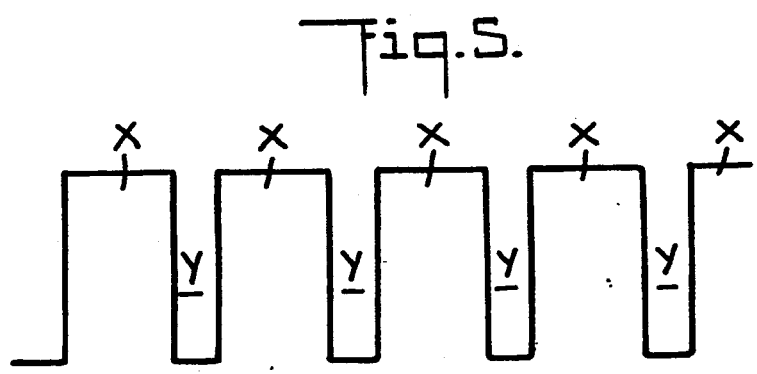
FIG. 5 shows the cyclical wave form produced by the timer included in the unit.

Unit 10 is provided with a direct-current power supply 25 whose output is applied to the stages of a unit through a cycle timer switch 26 so that the unit is activated only when the cycle timer switch is "on." The cycle timer switch operation is such as to cyclically activate the unit for a predetermined time period during which a corona discharge beam is produced, successive cycles being separated by a shorter relaxation interval during which the timer switch is off. As shown by the on-off wave in FIG. 5, each cycle X may have a 15-second "on" duration and each relaxation interval a 3-second "off" duration. In practice, other duty cycles may also be efficacious.

The reason for cyclically activating the unit is that during each inactive interval, the heat produced in the body tissue during the preceding active cycle is permitted to be propagated by heat conduction from the skin surface into the interior of the problem region, thereby reducing the skin temperature and avoiding overheating that may occur should the unit be on continuously for a prolonged period. The cyclical operation of the unit also prevents overheating of the unit itself should the unit be kept on continuously for a prolonged period.

The timer also makes it possible to meter the dosage applied to the patient, this being done by means of a digital counter 27 coupled to the timer. Counter 27 counts the number of timing cycles that occur; hence if each cycle has a 15-second duration, followed by a 5-second off interval, then the counter will count three "on" cycles per minute. If, therefore, the operator is instructed for a given treatment to apply a dosage of 10 cycles to a patient, he can readily do so. And the timer-counter arrangement also makes it possible to bill a patient on the basis of the number of cycles of treatment. The counter is resettable so that it is zero at the beginning of each treatment.

Gun 12 is provided with a grip 28 having a trigger switch 29 mounted thereon. This switch, one contact of which is grounded, is connected by a line 30 to power supply 25. In this way, the unit 10 is only turned on when an operator holding the gun 12 in his hand actuates the trigger switch. In practice, the trigger switch may be arranged to actuate a relay having a time delay characteristic, so that once the trigger is momentarily pulled, the unit is turned on for, say, a 15-second interval, and does not release until this interval is completed.

The applicator gun may be shaped like a typical hair blow dryer, and it is even lighter than such a dryer, for all it contains is the tank circuit and the discharge electrode. Because the operator is free to manipulate the gun which is connected to unit 10 by a long cable (say, 6 feet in length), he able to treat any region of an animal patient. In treating an animal such as a horse, the audio sound produced by the unit when a corona discharge takes place may startle the animal and make it difficult to treat the animal.

To avoid startling the animal, the unit may include a sound generator which produces a tone at the same frequency as that produced by the corona discharge beam, but somewhat louder. This sound generator can be switched on by the operator before subjecting the animal to treatment so that the animal becomes accustomed to this sound, and when the corona discharge beam is then turned on, its sound has no effect on the animal.

The Electrode

Figure 3:
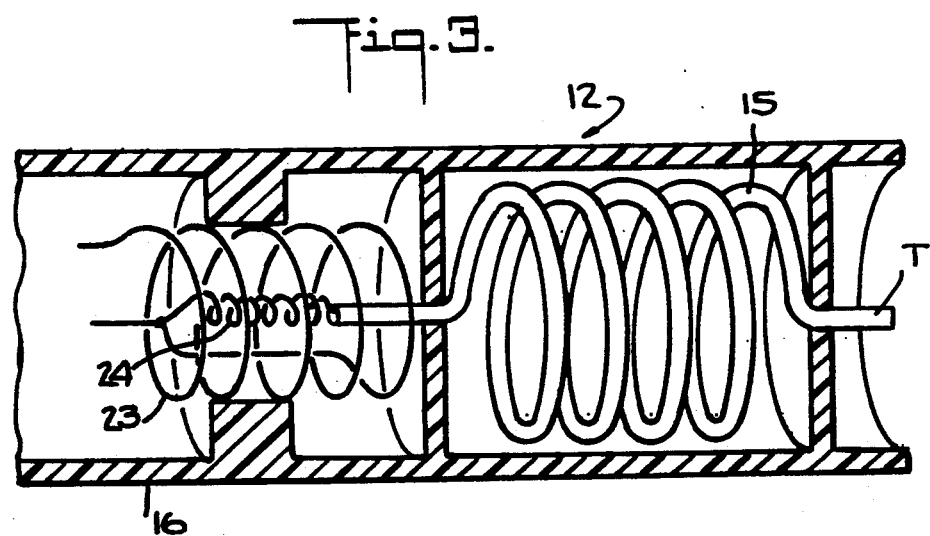
FIG. 3 is a section taken through the barrel of the gun, showing the components housed therein.

Electrode 15, as best seen in FIG. 3, instead of being a short length of straight rod or wire as in our copending application, is a wire of much greater length, such as 9 inches, which is formed into a helical coil, one end of which is connected to output coil 24 coupled inductively to tank coil 23, the other end T serving as the electrode tip.

Electrode 15 functions as a radiating antenna to match the impedance of the propagating medium, which in this case is air, to the source which in this case is the energy generating unit 10. To the extent to which an antenna fails to provide a good match, the energy delivered to the antenna will not be fully radiated.

The energy is radiated from the tip T of the antenna to create the corona discharge beam. We have found that spurious corona discharges emanate laterally from the convolutions of the helix, and that such undesirable emanations can be suppressed by spray coating these convolutions with an epoxy resin so that the corona discharge is confined to the tip.

The length of the wire from which the helical antenna is formed depends on the operating radio frequency of the unit, and the usual principles of antenna design and impedance matching applies to this length.

While there has been shown and described a preferred embodiment of a high-power corona discharge beam thermotherapy system in accordance with the invention, it will be appreciated that many changes and modifications may be made therein without, however, departing from the essential spirit thereof.

We claim:

1. A corona discharge beam thermotherapy system for veterinary applications adapted to project the beam onto the skin surface of an animal overlying a problem region, the beam serving to relieve pain, said system comprising:

(a) an energy-generating unit having a power exceeding 25 watts in which a radio-frequency carrier having a predetermined radio frequency is modulated by an audio-frequency signal having a predetermined audio frequency to produce at an output terminal periodic bursts of radio-frequency energy whose repetition rate corresponds to the frequency of the signal; and (b) a portable applicator gun having a relatively short barrel provided with an open mouth, in which barrel are housed both a tank circuit connected by a cable extending from the gun to the output terminal of the unit and a long discharge electrode, one end of which is coupled to the tank circuit, the other end of which terminates in a tip adjacent the mouth of the barrel, from which tip the energy is radiated to project said beam toward said skin surface which is spaced from the tip, said electrode having a helical coil form whereby it can be housed within said relatively short barrel.

2. A system as set forth in claim 1, wherein said unit is provided with a radio-frequency generator to produce said carrier, an audio-frequency oscillator to produce said signal, and means to modulate the carrier with said signal to produce the bursts of energy.

3. A system as set forth in claim 1, wherein said tank circuit includes a tank coil tuned to the frequency of the carrier and connected by said cable to said terminal, and an output coil inductively coupled to the tank coil and connected to the electrode which functions as an antenna whose impedance matches that of the tank coil.

4. A system as set forth in claim 1, in which said gun is provided with a grip having a trigger switch mounted thereon and connected by a line which runs along said cable to a power supply for said unit, whereby said unit is activated only when the trigger switch is actuated.

5. A system as set forth in claim 1, wherein said cable is coaxial cable whose outer conductor is grounded.

6. A system as set forth in claim 1, wherein said unit includes means generating a carrier whose frequency lies within a low radio-frequency range whose upper limit is about one million Hz.

7. A system as set forth in claim 1, wherein said unit includes a cycle timer switch means which cyclically activates said unit in the course of its operation to produce operating cycles having a predetermined duration, and an inactive interval between successive cycles of shorter duration.

8. A system as set forth in claim 7, wherein each cycle produced by said switch means has a duration of about 15 seconds and each interval a duration of no greater than about 5 seconds.

9. A system as set forth in claim 7, further including a counter coupled to the switch means to count the cycles produced by the switch means in the course of operation.

10. A system as set forth in claim 1, in which the coil has convolutions which are coated with an insulation layer to prevent spurious corona discharges therefrom.

11. A system as set forth in claim 10, in which the insulation layer is an epoxy coating.

* * * * *